(12) United States Patent
Hamilton et al.

(10) Patent No.: US 7,985,412 B2
(45) Date of Patent: Jul. 26, 2011

(54) METHOD OF MONITORING/CONTROLLING THYSANOPTERA

(75) Inventors: James Gordon Campbell Hamilton, Alderley Edge (GB); William Daniel John Kirk, Market Drayton (GB)

(73) Assignee: Keele University, Staffordshire (GB)

( * ) Notice: Subject to any disclaimer, the term of this patent is extended or adjusted under 35 U.S.C. 154(b) by 1476 days.

(21) Appl. No.: 11/205,873

(22) Filed: Aug. 17, 2005

(65) Prior Publication Data

US 2006/0041018 A1 Feb. 23, 2006

Related U.S. Application Data

(63) Continuation-in-part of application No. 10/499,531, filed on Oct. 28, 2004.

(51) Int. Cl.
*A01N 25/00* (2006.01)
*A01N 25/24* (2006.01)
*A01N 37/00* (2006.01)

(52) U.S. Cl. ........... 424/405; 424/407; 514/506

(58) Field of Classification Search ............ 424/405, 424/407; 514/506
See application file for complete search history.

(56) References Cited

U.S. PATENT DOCUMENTS

| | | | | |
|---|---|---|---|---|
| 4,017,030 A | * | 4/1977 | Coplan et al. | 239/44 |
| 5,634,292 A | * | 6/1997 | Kitterman | 43/115 |
| 2002/0061324 A1 | * | 5/2002 | Light et al. | 424/405 |

FOREIGN PATENT DOCUMENTS

| | | | |
|---|---|---|---|
| SU | 2581576 | * | 2/1978 |
| SU | 3656938 | * | 10/1983 |
| WO | WO 99 56538 | | 11/1999 |
| WO | WO 99 62334 | | 12/1999 |

OTHER PUBLICATIONS

Koschier et al. (Journal of Chemical Ecology, 2000, vol. 26, 2643-2655).*
Koschier, Elisabeth H. et al., "Assessing the attractiveness of volatile plant compounds to western flower trhips *Frankliniella occidentalis*", *Journal of Chemical Ecology*, vol. 26, No. 12, Dec. 2000, pp. 2643-2655.
Hooper et al., "Verbena x hybrida flower volatiles attractive to Western flower thrips, *Frankliniella occidentalis*", *Pesticide Science*, vol. 55, No. 6, 1999 pp. 660-662.
Bessonova et al., "Insecticide synergists in aerosol form" retrieved from STN, database accession No. 84:100816 XP002239736, & *Anoewandte Parasitologie* (1975), 16(3), pp. 147-152.

* cited by examiner

*Primary Examiner* — Sreeni Padmanabhan
*Assistant Examiner* — Mei-Ping Chui
(74) *Attorney, Agent, or Firm* — Woodard, Emhardt, Moriarty, McNett & Henry LLP

(57) ABSTRACT

A method of monitoring/controlling Thysanoptera (hereafter *thrips*) by the use of a behavior modifying compound of Formula (1), wherein Formula (1) is:—

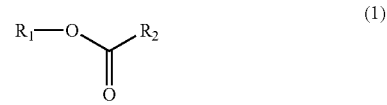

(1)

where $R_1$ is a monoterpenyl group and $R_2$ is a $C_3$-$C_5$ group.

46 Claims, No Drawings

METHOD OF MONITORING/CONTROLLING THYSANOPTERA

CROSS REFERENCE TO RELATED APPLICATIONS

This application is a continuation-in-part and claims priority from the U.S. patent application Ser. No. 10/499,531, filed Oct. 28, 2004, which is incorporated herein by reference in its entirety.

The present invention relates to a method of monitoring/controlling Thysanoptera (*thrips*), particularly but not exclusively for monitoring/controlling Western Flower *Thrips* (*Frankliniella occidentalis* (Pergande)).

Spoilage of cultivated plants/crops by insect pests is a widespread problem. Insects are recognised to cause direct damage by eating the plants/crops and also by laying eggs therein. Additionally insects often carry transferable diseases that cause damage of plants/crops.

One method of controlling insects is the direct application of pest control agents/pesticides to the plant/crop. However, as the pest control agents/pesticides used are commonly toxic to other animals their use is becoming increasingly less acceptable on environmental grounds. Also there is the problem of the triggering of undesirable reactions, such as poisoning or allergies, for agricultural and horticultural workers. Many consumers are reluctant to purchase edible crops that have been treated with pesticides, because of fears of adverse effects on their health from pesticide residues.

The use of traps in the vicinity of the crop that contain an attractant sex pheromone and a pest control agent is becoming increasingly widespread. The traps may be selective in attracting one sex (usually the male) of the insect concerned so as to remove them from the population and hence control population growth. Alternatively the traps may be more general in their operation.

The general release of an attracting sex pheromone is also sometimes used as a control measure. The released sex pheromone "confuses" the sex that is attracted so that it cannot locate a mate. This disruption of the mating process slows down or stops the build up of the pest population.

The Order Thysanoptera (*thrips*) is a group of insects that is recognised as causing damage to a wide range of cultivated crops. Some *thrips* are a pest of a particular crop, e.g. avocado *thrips* are a pest of avocado crops, whereas some species are a pest of a wide range of crops. *Thrips* cause damage to crops by feeding upon the crops and laying their eggs therein. Their feeding method comprises penetrating parts of the plant and sucking out the liquid contents, thus causing aesthetically unappealing scarring and stunting the growth of the crop. The presence of insects alone or small feeding marks can make ornamental crops unsaleable. Some *thrips* spread plant viruses, which can cause considerable damage to many crops.

*Thrips* are commonly active within enclosed parts of the crop, such as flower buds and leaf buds. Thus commonly the damage caused by *thrips*, in the form of direct damage such as feeding and in the form of indirect damage such as transmission of a virus, has often occurred before the *thrips* themselves have been observed. For crops such as commercially harvested flowering plants the management of *thrips* is a particularly acute problem as the *thrips* damage is sometimes only observed in the late stages of the flower development when the bud finally opens. *Thrips* are also a problem because they breed rapidly and large pest populations can build up very quickly if unchecked.

*Thrips* are difficult to control with insecticides because they retreat into minute recesses on the plant where insecticides are less likely to reach them and because the main pest species have high levels of insecticide resistance. Additionally pesticides applied to crops are perceived to be a poor solution to the problem of *thrips* since the pesticides used are normally detrimental to the population of beneficial arthropods that prey upon the *thrips* and other insect and mite pests on the crop.

Biological control agents such as predatory mites or fungal pathogens, are sometimes used to control *thrips*, but they are not always reliable and they are not very effective on some crops.

It is an object of the present invention to obviate and mitigate the problems outlined above.

According to the present invention there is provided a method of monitoring/controlling Thysanoptera (hereafter *thrips*) by the use of a behaviour modifying compound of Formula (1), wherein Formula (1) is:—

$$R_1-O\underset{\underset{O}{\|}}{\diagdown}R_2 \qquad (1)$$

where $R_1$ is a $C_8$-$C_{12}$ group and $R_2$ is a $C_2$-$C_8$ group.

The method of the present invention has been found to be particularly effective in mimicking the effects of a natural *thrips* pheromone and thus the *thrips* may be effectively attracted for monitoring or control purposes. They may also be confused for control purposes. The invention, therefore, does not rely on any toxic qualities of the compound of Formula (1) but rather on modification of *thrips*' behaviour for its effect.

When either sex of the *thrips* is attracted and monitored the method of the present invention may be used to gauge the population density of *thrips* in a particular area from analysis of the number and/or sex of the *thrips* caught. Based on the number of *thrips* attracted a decision may then be made as to what further action, if any, is required. At an extreme level the level of monitoring may be selected so that as high a portion of the number of *thrips* are removed from the population as possible.

When female *thrips* are attracted and monitored, management of the overall *thrips* population is achieved as the number of female *thrips* is reduced. It has been observed that when the method of the invention is used to attract and monitor female *thrips* it is particularly efficacious as with removal of a portion of the number of egg-laying females from the *thrips* population not only is the damage caused by females laying eggs in a crop to be protected quickly reduced but also population growth is quickly curbed with its associated advantages in terms of reduced damage.

When male *thrips* are attracted and monitored management of the overall *thrips* population is achieved as the female *thrips* are not fertilised. Unfertilised females then produce only male *thrips* thus the number of females in the next generation is reduced and so population increase is curbed.

$R_1$ is preferably aromatic, aliphatic or cycloaliphatic. $R_1$ may be a cyclic or a multi-cyclic (e.g. a bi-cyclic) moiety.

It is preferred that $R_1$ is $C_9$-$C_{11}$ and most preferably $C_{10}$.

A preferred form of $R_1$ is monoterpenyl.

Most preferably $R_1$ is isobornyl, as shown below.

Alternatively $R_1$ may be a lavandulyl group.
Alternatively $R_1$ may be a neryl group.
$R_2$ is preferably straight or branched alkyl or alkylene.

It is preferred that $R_2$ is $C_3$-$C_5$ and most preferably $C_4$ (i.e. the $R_2C(O)O$ group in the compound of Formula (1) has a total of 5 carbon atoms).

Suitable examples of the $R_2 C(O)O$ group in the compound of Formula (1) are the valerate, isovalerate, 2-methyl butanoate (particularly (S)-2-methylbutanoate) and pivalate groups.

The compound of Formula (1) may be isobornyl valerate, i.e.:—

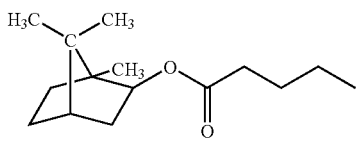

Alternatively the compound of Formula (1) may be isobornyl isovalerate, isobornyl 2-methyl butanoate or isobornyl pivalate. Further possibilities include lavandulyl valerate, lavandulyl isovalerate, lavandulyl 2-methyl butanoate and lavandulyl pivalate.

In a preferred embodiment of the invention, the compound of Formula (1) may be neryl (S)-2-methylbutanoate which we have found to be a male-produced aggregation pheromone in Western Flower *Thrips*.

The method of the invention, i.e. the way in which the compound of Formula (1) is used, may be carried out in several ways. For a method of controlling *thrips* these include use as a confusant.

In this method a compound of Formula (1) is broadcast within an area infested (or potentially infested) by *thrips*. As the compound of Formula (1) mimics the effect of a *thrips* pheromone the *thrips* become "confused", namely the application of a compound of Formula (1) overcomes the effect of any natural *thrips* pheromones present with the result that the *thrips* cannot find a mating partner.

For a method of monitoring *thrips* a compound of Formula (1) may be provided in a release device located in an area infested (or potentially infested) by *thrips*. The release device may include a means for immobilising and/or killing the *thrips* so that the *thrips* cannot leave the release device once attracted thereto. Namely the release device may be used as a pest control device by attracting and then removing *thrips* from an area.

Preferably the compound of Formula (1) is held in/on a support of the release device. Generally the support medium is an adhesive material so that the *thrips* stick thereto.

One preferred example of a release device comprises a sheet of plastic having a sticky adhesive coating which has been soaked/coated with a formulation including a compound of Formula (1). Such release devices are commonly referred to as "Sticky Traps". Preferably the plastic is porous to allow penetration of said formulation. Generally the solvent for said formulation is hexane or acetone. As *thrips* are attracted to certain colours the sticky paper is preferably coloured to act as a secondary attractant. Most preferably the sheet of sticky plastic is coloured blue, white or yellow. The use of coloured release devices is described in the paper *Zeitschrift für Angewandte Entomologie* 107, 136-140 (H. F. Brødsgaard). In this paper a sheet having a colour close to Pantone® 279 (a shade of blue) was found to be the most attractive for *thrips*.

Generally each sheet of plastic is rectangular having dimensions of around 7 cm and between 10-15 cm, although sheets of other sizes are not precluded. For example the sheet may be in the form of a strip and extend around/across a portion of the growing area.

A further preferred example of a release device comprises a container that is filled with a mixture of water and detergent and a small piece of rubber or plastic soaked/coated with a formulation including a compound of Formula (1). Such release devices are commonly referred to as "Water Traps". Most preferably the container is coloured blue, white or yellow.

Whilst it is to be appreciated that the method of the present invention may be applied to monitor *thrips* in a variety of different locations it is preferred that the method of the present invention is used in an enclosed structure such as a greenhouse. In this case the release device is preferably in the form of a strip extending along a side of the greenhouse.

When used in an enclosed structure it is preferred that each release device produces/releases an effective amount of the compound of Formula (1). Generally in order to produce/mimic the effect of a single *thrips* the release device is configured to produce/release a compound of Formula (1) in an amount which is at least and more preferably a multiple of the amount of pheromone which would be released by a single *thrips*. The preferred release rate of a release device is in the region of from 150 to 1,500,000 picograms (1.5 µg) per hour with more preferably 1000 to 750,000 picograms (0.75 µg) per hour and most preferably 2000 to 300,000 picograms (0.3 µg) per hour.

Preferably the method of the present invention is used to monitor/control the population of *thrips* for cultivated flower crops, e.g. chrysanthemums and roses and additionally for other crops such as cucumbers and peppers.

It is proposed that the method of the present invention may be used to monitor/control walking and/or flying species of *thrips*. Preferred examples of such *thrips* include *Thrips palmi* (Karny), *Thrips tabaci* (Lindeman), *Frankliniella fusca* (Hinds), *Frankliniella schultzei* (Trybom), *Frankliniella tritici* (Fitch) and Western Flower *Thrips* (*Frankliniella occidentalis*). Most preferably the method of the present invention is used to control the population of Western Flower *Thrips* (*Frankliniella occidentalis*).

The invention will be now be further described with reference to the following non-limiting Examples.

LABORATORY EXAMPLES

Rearing *Thrips*

*Thrips* were originally obtained from a commercial glasshouse and then maintained on pot chrysanthemums (*Dendranthema* x *grandiflora* (Ramat.) Kitamura) at 25° C. under a repeated cycle consisting of 18 hours of light and 6 hours of dark. The culture on chrysanthemums supplied mixed-age adult females, which were attracted to adult males in olfactometer bioassays, so these were used in the bioassays.

The Y-tube Olfactometer

The Y-tube has two branches at an angle of 90° and a stem, which are all 60 mm long with internal diameters of 5 mm. The Y-tube was held horizontal and illuminated from above by four fluorescent tubes (950 lux). It was screened by a 10 cm high matt-black card wall, forming a 280 mm×280 mm square, to minimise any external visual influences. A 50 ml round glass flask with a Drechsel head was inserted in the tube before each branch and a semi-circle of filter paper (Whatman No. 1, diameter 42.5 mm), moistened with water, was placed in each to humidify the air. Connections between tubes were either made with brass swagelock connectors or by inserting narrower tubes into slightly wider tubes. All the glassware and the glass wool were rinsed thoroughly in warm water with Teepol 'L' neutral detergent (BDH Laboratory Supplies, Poole), then in distilled water, then in acetone, and left to dry overnight in an oven at 200° C. before each experiment. The connecting Teflon tubing and the swagelock connectors were rinsed thoroughly in warm water with Teepol 'L' neutral detergent, then in distilled water, then in hexane, and left to dry overnight in a fume cupboard before each run of an experiment.

Zero-grade clean air from a cylinder (supplied by British Oxygen Corporation, Manchester) was passed through an activated charcoal filter and then along Teflon tubes to two flow meters (Supelco, Sigma-Aldrich, Poole) that regulated the air flow to the two branches of a glass Y-tube. The rate in the two branches was 50 mm s$^{-1}$ (59 ml min$^{-1}$) and in the stem was 100 mm s$^{-1}$ (118 ml min$^{-1}$) and were checked with a bubble flow meter.

Y-tube Olfactometer Bioassays

Adults were placed one at a time in the stem of the Y-tube, by transferring them with a fine paintbrush, and allowed to walk up the Y-tube. A choice was recorded when they first crossed a line 20 mm down either branch from the junction of the "Y". If a choice was not made within 3 min, it was recorded as "no choice" and excluded from the analysis. Each individual was tested twice to provide two successive choices. The sample flasks, connecting tubing and Y-tube were reversed after every 5 individuals. This reduced possible bias from external influences. Each experiment consisted of 1 to 3 runs on separate days to reduce possible bias from external influences. A total of 25 individuals were tested in each run of an experiment, which lasted about 2 h. Experiments were conducted at 25±1° C.

At the start of each run, 0.2 ml of distilled water was placed on the filter paper in each flask. 1 μl of the test substance (a known amount in hexane) was placed on the filter paper in one flask and 1 μl of hexane was placed on the filter paper in the other flask as a control. The filter papers were removed and replaced with fresh water and test and control substances every time the equipment was reversed.

It was shown that there was no preference in *thrips* response by testing mixed-age females (in the absence of a test composition) in the Y-tube olfactometer on 3 separate days. The apparatus was set up as before, but with only water and hexane in each flask. Since the arms of the Y-tube were reversed by rotating the stem by 180° after every five individuals, the difference in the number of choices between left and right and between arm A and arm B could be tested separately. There was no preference to the left or right or for arm A or arm B thus establishing that the apparatus was unbiased.

Results

Example 1

Using the method outlined above the compound isobornyl valerate (shown below), which was synthesised in the laboratory from isobornyl alcohol and valeric acid,

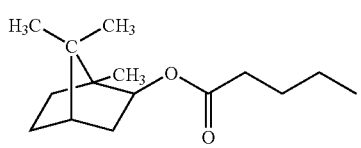

applied in a Y-tube olfactometer was found to be an attractant for female Western Flower *Thrips*. In each case 25 adult females were tested in 2 or 3 separate runs. The compound was applied in 1 μl hexane. The results were combined from the separate runs and are shown in Table 1. Also for each result in Table 1 a figure showing the probability of this result happening merely by chance is shown.

TABLE 1

| Amount of Compound (ng) | Solvent | Preference (%) | Probability |
|---|---|---|---|
| 0.002 | Hexane | 64.8 | 0.007 |
| 0.02 | Hexane | 73.3 | <0.0001 |
| 0.1 | Hexane | 76.9 | <0.0001 |
| 0.2 | Hexane | 79.8 | <0.0001 |
| 2 | Hexane | 60.3 | 0.026 |

In each case it can be seen that the probability of the result merely occurring by chance is extremely unlikely. In each case the *thrips* tested can be seen to exhibit a strong preference for the compound isobornyl valerate (shown schematically above). Thus it can be concluded that isobornyl valerate is a strong attractant for *thrips*.

Example 2

Example 1 was repeated using each of isobornyl 2-methyl butanoate, isobornyl pivalate and lavandulyl valerate in amounts of 0.1 ng. The method was modified slightly so that the filter paper was placed in a length of Teflon tube instead of in a glass flask. The results obtained were as follows:

| Compound | Preference (%) | P |
|---|---|---|
| Isobornyl 2-methyl butanoate | 72.9% | 0.018 |
| isobornyl pivalate | 61.3% | 0.010 |
| lavandulyl valerate | 79.2% | <0.001 |

It can be seen from the above data that each of the above three compounds is a strong attractant for the *thrips*.

Comparative Example 1

Using the method outlined above the compound (lavandulyl acetate) shown below

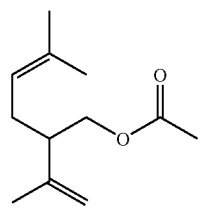

applied at doses of 0.1 ng, 1 ng, 10 ng, 100 ng and 1000 ng (where ng is nanogram) under the conditions outlined above showed no attractant effect upon female Western Flower *Thrips*.

Comparative Example 2

Using the method outlined above the compounds shown below
$CH_3CO_2CH_2CHC(CH_3)CH_2CH_2CHC(CH_3)_2$ Neryl Acetate and
$HCO_2CH_2CHC(CH_3)CH_2CH_2CHC(CH_3)_2$ Neryl Formate
applied at doses of 1 ng, long, and 100 ng under the conditions outlined above showed no effect upon female Western Flower *Thrips*.

Field Trial

Example 3

The biological activity of neryl (S)-2 methylbutanoate was tested in commercial crops of sweet pepper (var. *Habana*) grown in greenhouses at Zamora (37°42.945'N, 0°57.720'W) near Torre Pacheco in the Murcia region of Spain. The crops were about 110 cm high, planted in rows 1 m apart, and were naturally infested with a low level of *F. occidentalis*. Three 2-day long experiments were carried out, alternating between two nearby houses, each with an area of about 6500 m².

The compound was released from rubber septa (6.3 mm diameter×10.8 mm long) (100706; Aldrich, UK) that had been preextracted in hexane-dichloromethane and dried in an oven at 50° C. Septa were loaded with solutions of the test compound in hexane or with hexane alone (control). After evaporation of the solvent, the rubber septa were stored in aluminum foil bags. They were placed on traps in the field within 2 hr of preparation.

Blue plastic rectangular takitraps (10×25 cm) (Syngenta Bioline, UK), coated on both surfaces with insect glue, were suspended vertically with the base about 10 cm above crop height, by attaching them to crop support strings with a wooden clothes peg. One rubber septum was stuck to the center of the north-facing side of each trap.

Each experiment was laid out in a randomized complete block design with 20 blocks and one replicate per block. Traps were placed about 3.4 m apart down rows of sweet pepper plants with 16 m between each row of traps. The experiment compared two doses, 30 ng and 30 µg, of neryl (S)-2-methylbutanoate with a control.

*Thrips* caught on the blue sticky traps were examined under a stereoscopic microscope to identify their sex and to distinguish *F. occidentalis* from about 2% of the *thrips* that were other species (*Thrips* spp., aeolothripids, and phlaeothripids). The data were $log_{10}(x+1)$ transformed and analyzed by two-way ANOVA for females, males, and both sexes combined. Multiple comparisons with the control used Dunnett's multiple comparison test. Statistical analysis was carried out with Minitab 14 (Minitab Inc., Pennsylvania, USA).

The results are shown in Table 2.

TABLE 2

MEAN CATCH OF ADULT *F. occidentalis* ON BLUE STICKY TRAPS WITH NERYL (S)-2-METHYLBUTANOATE [N(S)2MB]

| | | Mean catch over 2 days ± SE (N = 20) | | |
|---|---|---|---|---|
| Compound | Thrips | Control | Low dose | High dose |
| N(S)2MB[a,b] | Females | 5.9 ± 0.7 | 6.8 ± 0.7 ns | 9.1 ± 1.2* |
| | Males | 9.5 ± 0.8 | 11.9 ± 1.2 ns | 13.2 ± 1.1** |
| | Both sexes | 15.4 ± 1.2 | 18.7 ± 1.7 ns | 22.2 ± 2.0*** |

[a]Of the compound, 30 ng is for low dose and 30 µg is for high dose.
[b]Dunnett's test comparing each dose with corresponding control using $log_{10}(x + 1)$ transformed data: *P < 0.05; P < 0.01; *P < 0.001.

As shown in the above Table, neryl (S)-2-methylbutanoate increased trap catches significantly at a dose of 30 µg. Both sexes were attracted, and the effect was similar for both females and males.

The invention claimed is:

1. A method of monitoring or controlling Thysanoptera (hereafter thrips) comprising providing to an area infested by or at risk of infestation by *thrips* a behavior modifying compound of Formula (1), wherein Formula (1) is:

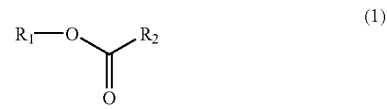

(1)

where $R_1$ is a monoterpenyl group and $R_2$ is a $C_3$-$C_5$ group.

2. The method according to claim 1, wherein $R_1$ is an isobornyl group.

3. The method according to claim 1, wherein $R_1$ is a lavandulyl group.

4. The method according to claim 1, wherein R1 is a neryl group.

5. The method according to claim 1, wherein $R_2$ is a straight or branched alkyl or alkylene.

6. The method according to claim 1, wherein $R_2$ is a $C_4$ group.

7. The method according to claim 1 wherein the $R_2$—C(O)O— group in the compound of Formula (1) is a valerate, isovalerate, pivalate or 2-methyl butanoate group.

8. The method according to claim 6 wherein the $R_2$—C(O)O— group in the compound of Formula (1) is a (S)-2-methylbutanoate group.

9. The method according to claim 7 wherein the compound of Formula 1 comprises one or more members selected from the group consisting of isobornyl valerate, isobornyl isovalerate, isobornyl pivalate, isobornyl 2-methyl butanoate, lavandulyl valerate, lavandulyl isovalerate, lavandulyl pivalate, and lavandulyl 2-methyl butanoate.

10. The method according to claim 1, wherein the compound of Formula (1) is provided in a release device located in an area infested by or at risk of infestation by thrips.

11. The method according to claim 10, wherein the release device includes a means for immobilizing or killing the *thrips*.

12. The method according to claim 11, wherein the compound of Formula (1) is held in or on a support medium of the release device.

13. The method according to claim 12, wherein the support medium is an adhesive material.

14. The method according to claim 13, wherein the release device comprises a sheet of plastic having a sticky adhesive coating which has been soaked or coated with a formulation including a compound of Formula (1).

15. The method according to claim 14, wherein the plastic is porous.

16. The method according to claim 14, wherein the sheet of plastic has been soaked or coated with a formulation comprising a compound of Formula (1) and hexane or acetone.

17. The method according to claim 14, wherein the plastic is colored blue, white or yellow.

18. The method according to claim 10, wherein the release device provides from 150 picograms per hour to 1,500,000 picograms (1.5 µg) per hour of a compound of Formula (1).

19. The method according to claim 18, wherein the release device provides from 1000 picograms per hour to 750,000 picograms (0.75 μg) per hour of a compound of Formula (1).

20. The method according to claim 19, wherein the release device provides from 2000 picograms per hour to 300,000 picograms (0.3 μg) per hour of a compound of Formula (1).

21. The method according to claim 1, wherein the method is used to control the population of *thrips* for edible or ornamental crops.

22. The method according to claim 1, wherein the compound of Formula (1) is provided by broadcasting said compound in an area infested by or at risk of infestation by *thrips*.

23. A device for providing a behavior modifying compound to an area infested by or at risk of infestation by Thysanoptera (hereafter *thrips*), said device comprising a compound of Formula (1) and being adapted to broadcast or release the compound of Formula (1) in said area, wherein Formula (1) is:

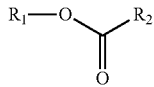

where $R_1$ is a monoterpenyl group and $R_2$ is a $C_3$-$C_5$ group.

24. The device according to claim 23, wherein said device is a release device.

25. The device according to claim 23, wherein said device is effective for broadcasting the compound of Formula (1) in said area.

26. The device according to claim 23, wherein $R_1$ is an isobornyl group.

27. The device according to claim 23, wherein $R_1$ is a lavandulyl group.

28. The device according to claim 23, wherein $R_1$ is a neryl group.

29. The device according to claim 23, wherein $R_2$ is a straight or branched alkyl or alkylene.

30. The device according to claim 23, wherein $R_2$ is a $C_4$ group.

31. The device according to claim 23 wherein the $R_2$—C(O)O— group in the compound of Formula (1) is a valerate, isovalerate, pivalate or 2-methyl butanoate group.

32. The device according to claim 23 wherein the $R_2$—C(O)O— group in the compound of Formula (1) is a (S)-2-methylbutanoate group.

33. The device according to claim 23 wherein the compound of Formula (1) comprises one or more members selected from the group consisting of isobornyl valerate, isobornyl isovalerate, isobornyl pivalate, isobornyl 2-methyl butanoate, lavandulyl valerate, lavandulyl isovalerate, lavandulyl pivalate, and lavandulyl 2-methyl butanoate.

34. The device according to claim 23, wherein the compound of Formula (1) is neryl(S)-2-methylbutanoate.

35. The release device according to claim 24, wherein the release device includes a means for immobilizing or killing the *thrips*.

36. The release device according to claim 24, wherein the compound of Formula (1) is held in or on a support medium of the release device.

37. The release device according to claim 36, wherein the support medium is an adhesive material.

38. The release device according to claim 24, wherein the release device comprises a sheet of plastic having a sticky adhesive coating which has been soaked or coated with a formulation including a compound of Formula (1).

39. The release device according to claim 38, wherein the plastic is porous.

40. The release device according to claim 38, wherein the plastic is colored blue, white or yellow.

41. The release device according to claim 24, wherein the release device is a sticky trap.

42. The release device according to claim 24, wherein the release device comprises a container that can be filled with a mixture of water and detergent; and a piece of rubber or plastic to which a compound of Formula (1) has been applied.

43. The release device according to claim 24, wherein the release device is a water trap.

44. The device according to claim 23, wherein the device provides from 150 picograms per hour to 1,500,000 picograms (1.5 μg) per hour of a compound of Formula (1).

45. The device according to claim 44, wherein the device provides from 1000 picograms per hour to 750,000 picograms (0.75 μg) per hour of a compound of Formula (1).

46. The device according to claim 45, wherein the device provides from 2000 picograms per hour to 300,000 picograms (0.3 μg) per hour of a compound of Formula (1).

* * * * *

UNITED STATES PATENT AND TRADEMARK OFFICE
CERTIFICATE OF CORRECTION

| | |
|---|---|
| PATENT NO. | : 7,985,412 B2 |
| APPLICATION NO. | : 11/205873 |
| DATED | : July 26, 2011 |
| INVENTOR(S) | : James Gordon Campbell Hamilton et al. |

Page 1 of 1

It is certified that error appears in the above-identified patent and that said Letters Patent is hereby corrected as shown below:

On the title page:
In Column 1, under the "Related U.S. Application Data" section, please replace with the following paragraph:

--Continuation-in-part of application No. 10/499,531, filed on Oct. 28, 2004, filed as 371 of international application No. PCT/GB02/05895, filed on December 23, 2002.--

After the above paragraph, please insert a new section entitled "Foreign Application Priority Data" and insert the following paragraph:

--Dec. 21, 2001 (GB) 0130577.0--

Signed and Sealed this
Eighth Day of November, 2011

David J. Kappos
*Director of the United States Patent and Trademark Office*